United States Patent [19]

Cherney et al.

[11] Patent Number: 5,359,070

[45] Date of Patent: Oct. 25, 1994

[54] UNSYMMETRICAL BIS-IMIDES AS ANTICANCER AGENTS

[75] Inventors: Robert J. Cherney, Newark; Steven P. Seitz, Swarthmore, both of Del.

[73] Assignee: The Du Pont Merck Pharmaceutical Company, Wilmington, Del.

[21] Appl. No.: 16,555

[22] Filed: Feb. 11, 1993

[51] Int. Cl.$^5$ .................. C07D 221/18; A61K 31/435
[52] U.S. Cl. ........................................ 546/76; 546/98
[58] Field of Search .................. 514/284; 546/78, 76

[56] References Cited

U.S. PATENT DOCUMENTS

| | | | |
|---|---|---|---|
| 4,146,720 | 3/1979 | Roldan et al. | 546/99 |
| 4,841,052 | 6/1989 | Harnisch et al. | 546/99 |
| 4,874,863 | 10/1989 | Brana et al. | 546/99 |
| 4,919,848 | 4/1990 | Harnisch | 546/99 |
| 5,086,059 | 2/1992 | Ardecky et al. | 514/284 |
| 5,206,249 | 4/1993 | Sun | 546/99 |
| 5,206,250 | 4/1993 | Sun | 546/99 |

FOREIGN PATENT DOCUMENTS 0281902  9/1988  European Pat. Off. .

OTHER PUBLICATIONS

Mattern, Canc. & Metastasis Rev vol. 7, pp. 263–284 (1988).

*Primary Examiner*—Donald G. Daus
*Attorney, Agent, or Firm*—Blair Q. Ferguson

[57] ABSTRACT

This invention relates to unsymmetrical bis-imide compounds, and pharmaceutically acceptable salts thereof, of the formula (i):

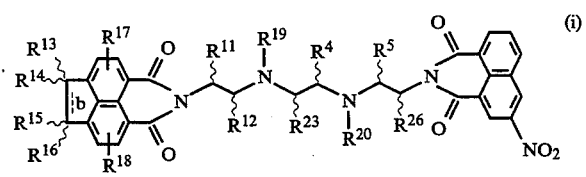

including (R,R)-1-[2-(acenaphthene-5,6-dicarboximido) propylamino]-2-[2-(3-nitronaphthalene-1,8-dicarboximido) propylamino]ethane, processes for the preparation of such compounds, pharmaceutical compositions containing such compounds, and methods of using such compounds to treat cancer, particularly solid tumor carcinomas, in mammals.

4 Claims, No Drawings

UNSYMMETRICAL BIS-IMIDES AS ANTICANCER AGENTS

FIELD OF THE INVENTION

This invention relates to unsymmetrical bis-imide compounds, and pharmaceutically acceptable salts thereof, of the formula (i):

[Chemical structure of formula (i)]

including (R,R)-1-[2-(acenaphthene-5,6-dicarboximido) propylamino]-2-[2-(3-nitronaphthalene-1,8-dicarboximido) propylamino]ethane, processes for the preparation of such compounds, pharmaceutical compositions containing such compounds, and methods of using such compounds to treat cancer, particularly solid tumor carcinomas, in mammals.

BACKGROUND OF THE INVENTION

Harnisch et al., U.S. Pat. No. 4,841,052 describe naphthalic acid imides useful as charge-regulating substances in electrophotographic toners.

Brana et al., U.S. Pat. No. 4,874,863 discloses anticancer bisnaphthalimides wherein the naphthalimides are linked by a straight chain or branched $C_4$-$C_{10}$-alkylene which is interrupted at one or two points in the chain by a secondary or tertiary amino group, where 2 nitrogen atoms may additionally be bonded to one another by an alkylene group. Brana et al., U.S. Pat. No. 4,874,863 does not disclose or suggest the unsymmetrical bis-imide compounds of the present invention. Moreover, the compounds of the present invention exhibit unexpected superior antitumor activity relative to the compounds specifically disclosed by Brana et al.

Ardecky et al. U.S. Pat. No. 5,086,059 discloses certain symmetrical bis-imide compounds. Ardecky et al. does not disclose or suggest the unsymmetrical bis-imide compounds of the present invention.

Sun PCT WO 92/17453 also discloses symmetrical naphthalimide compounds. Sun does not disclose or suggest the unsymmetrical compounds of the present invention. Moreover, the compounds of the present invention have unexpected improved solubility relative to the compounds of Sun.

DETAILED DESCRIPTION OF THE INVENTION

There is provided by this invention bis-imide compounds, and pharmaceutically acceptable salts thereof, having the formula (i):

[Chemical structure of formula (i)]

and enantiomeric or diastereomeric forms thereof, or mixtures of enantiomeric or diastereomeric forms thereof, wherein:

$R^{11}$, $R^{12}$, $R^{19}$, $R^{20}$, $R^{23}$, $R^4$, $R^5$, and $R^{26}$ are independently selected from H, $CH_3$, and $CH_2CH_3$;

$R^{13}$, $R^{14}$, $R^{15}$, $R^{16}$, $R^{17}$, and $R^{18}$ are independently selected from: H, $S(O)_nR^{21}$, $C_1$-$C_6$ alkyl, $C_1$-$C_6$ alkenyl, trihalomethyl, aryl, halogen, $C_1$-$C_6$ alkoxy, hydroxy, amino, $C_1$-$C_6$ di- or monoalkylamino, $C_1$-$C_6$ alkylcarbonyl, $C_1$-$C_7$ carboalkoxy, formyl, cyano, nitro; and $R^{21}$ is selected from $C_1$-$C_6$ alkyl or aryl;

n is 0, 1, or 2;

b, the bond between carbon atoms substituted with $R^{13}$ and $R^{15}$, may be a single or double bond; when b is a double bond, $R^{13}$ and $R^{15}$ are substituted as stated above, and $R^{14}$ and R16 do not exist.

The present invention includes the above-described compounds of formula (i), and pharmaceutically acceptable salts thereof, and enantiomeric or diastereomeric forms thereof, or mixtures of enantiomeric or diastereomeric forms thereof, wherein:

$R^{11}$, $R^{12}$, $R^{23}$, $R^4$, $R^5$ and $R^{26}$ are independently selected from H and $CH_3$;

$R^{19}$ and $R^{20}$ are H;

$R^{13}$, $R^{14}$, $R^{15}$, $R^{16}$, $R^{17}$, and $R^{18}$ are independently selected from: H, $S(O)_nR^{21}$, $C_1$-$C_6$ alkyl, $C_1$-$C_6$ alkenyl, trihalomethyl, aryl, halogen, $C_1$-$C_6$ alkoxy, hydroxy, amino, $C_1$-$C_6$ di- or monoalkylamino, $C_1$-$C_6$ alkylcarbonyl, $C_1$-$C_7$ carboalkoxy, formyl, cyano, nitro; and $R^{21}$ is selected from $C_1$-$C_6$ alkyl or aryl;

n is 0, 1, or 2;

b, the bond between carbon atoms substituted with $R^{13}$ and $R^{15}$, may be a single or double bond; when b is a double bond, $R^{13}$ and $R^{15}$ are substituted as stated above, and $R^{14}$ and $R^{16}$ do not exist.

Preferred compounds of the present invention include those compounds described above of formula (i) wherein:

$R^{11}$ and $R^{26}$ are $CH_3$;

$R^{12}$, $R^{23}$, $R^4$, and $R^5$ are H;

$R^{19}$ and $R^{20}$ are H;

b is a single bond; and $R^{13}$, $R^{14}$, $R^{15}$, $R^{16}$, $R^{17}$, and $R^{18}$ are H.

The present invention includes the following compounds, and pharmaceutically acceptable salts thereof:

(R,R)-1-[2-(acenaphthene-5,6-dicarboximido) propylamino]-2-[2-(3-nitronaphthalene-1,8-dicarboximido) propylamino]ethane;

(S,S)-1-[2-(acenaphthene-5,6-dicarboximido) propylamino]-2-[2-(3-nitronaphthalene-1,8-dicarboximido) propylamino]ethane;

(racemate+meso)-1-[2-(acenaphthene-5,6-dicarboximido) propylamino]-2-[2-(3-nitronaphthalene-1,8-dicarboximido) propylamino]ethane;

(meso)-1-[2-(acenaphthene-5,6-dicarboximido) propylamino]-2-[2-(3-nitronaphthalene-1,8-dicarboximido) propylamino]ethane.

A representative compound of the present invention is the following:

(R,R)-1-[2-(acenaphthene-5,6-dicarboximido) propylamino]-2-[2-(3-nitronaphthalene-1,8-dicarboximido)propylamino]ethane dihydromethanesulfonate, (Ib).

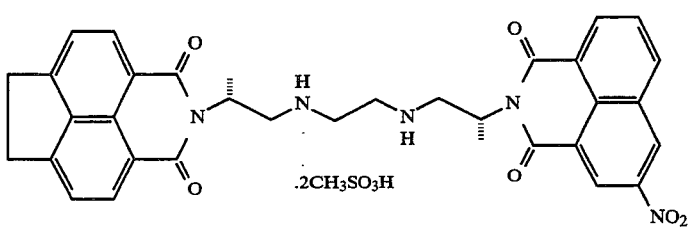

Ib

Also provided by this invention are processes for the preparation of the above described compounds of formula (i), pharmaceutical compositions comprising the such compounds of formula (i) and a pharmaceutically acceptable carrier, and methods of using these compounds for the treatment of cancer, particularly solid tumor carcinomas, in a mammal.

The compounds herein described may have asymmetric centers. All chiral, diastereomeric, and racemic forms are included in the present invention. Any geometric isomers which be present in the compounds described herein, and all such stable isomers are contemplated in the present invention. All chiral, diastereomeric, racemic forms and all geometric isomeric forms of a structure are intended, unless the specific stereochemistry or isomer form is specifically indicated.

When any variable (for example, $R^{21}$) occurs more than one time in any constituent or in formula (i) or any other formula herein, its definition on each occurrence is independent of its definition at every other occurrence.

Combinations of substituents and/or variables in a chemical structure are permissible only if such combinations result in stable compounds.

When a bond to a substituent is shown to cross the bond connecting two atoms in a ring, then such substituent may be bonded to any atom on the ring.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Alkenyl" is intended to include hydrocarbon chains of either a straight or branched configuration and one or more unsaturated carbon-carbon bonds which may occur in any stable point along the chain, such as ethenyl, propenyl, and the like. "Halo" or "halogen" as used herein refers to fluoro, chloro, bromo, and iodo; and "counterion" is used to represent a negatively charged species such as chloride, bromide, hydroxide, acetate, sulfate, and the like. As used herein, "aryl" or "aromatic residue" is intended to mean phenyl or naphthyl The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, and phthalyl; 2) sulfonyl, including substituted aryl sulfonyl groups such as p-toluenesulfonyl; 3) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 4) aliphatic carbamate types such as tert-butyloxycarbonyl (Boc), ethoxycarbonyl, diisopropylmethoxycarbonyl, and alyloxycarbonyl; 5) cyclic alkyl carbamate types such as cyclopentyloxycarbonyl and adamantyloxycarbonyl; 6) alkyl types such as triphenylmethyl and benzyl; 7) trialkylsilane such as trimethylsilane; and 8) thiol containing types such as phenylthiocarbonyl and dithiasuccinoyl.

Brana et al. U.S. Pat. No. 4,874,863, Sun PCT Patent Application Publication Number WO 92/17453, and U.S. Pat. No. 5,086,059 do not describe the synthesis of unsymmetrical bis-imides, such as those presently claimed. Moreover, the compounds of the present invention were discovered to have greatly increased antitumor activity relative to the compounds specifically disclosed in Brana et al. U.S. Pat. No. 4,874,863.

SYNTHESIS

Compounds of the present invention can be synthesized using the methods described below, together with synthetic methods known in the art of synthetic organic chemistry. The references cited below are all incorporated herein by reference.

The free base of a compound of the present invention can be acidified with the appropriate mineral or organic acid in ethanol or dichloromethane, for example, to produce a pharmaceutically acceptable salt. Generally, pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference. The free base of the compounds of formula (i) may require purification by techniques such as column chromatography, recrystallation, or distillation for example, as well as other techniques well known to those skilled in the art of organic synthesis before its salt can be prepared as described above.

Procedures for the synthesis of the diastereomeric or enantiomeric forms of the polyamine linker in compounds of formula (i) of the present invention, or mixtures of enantiomeric or diastereomeric forms thereof, are described in Sun, PCT Patent Application Publication Number WO 92/17453.

Compounds of formula (i) may be synthesized in two ways, differing only in the order in which the anhydrides are condensed, as shown in Scheme A. In Scheme A, the nitrogen atoms of the polyamine linker are shown as NH, the nitrogen atoms may be optionally substituted with methyl or ethyl. As shown in Scheme A, the synthesis begins with the condensation of polyamine (iii) ($R^9$ is an amine protecting group as described above, preferably a substituted arylsulfonyl amine protected group, for example, mesitylenesulfonyl) with either anhydride (iv) or anhydride (v). This yields the mono-imide (vii) or (viii), respectively. The sulfonamide can be removed from the mono-imide through the action of HBr/acetic acid to yield the free base (ix) from (vii) or the free base (x) from (viii). The synthesis of compounds of formula (i) is completed by condensation of anhydride (v) onto free base (ix) or by the condensation of anhydride (iv) onto free base (x).

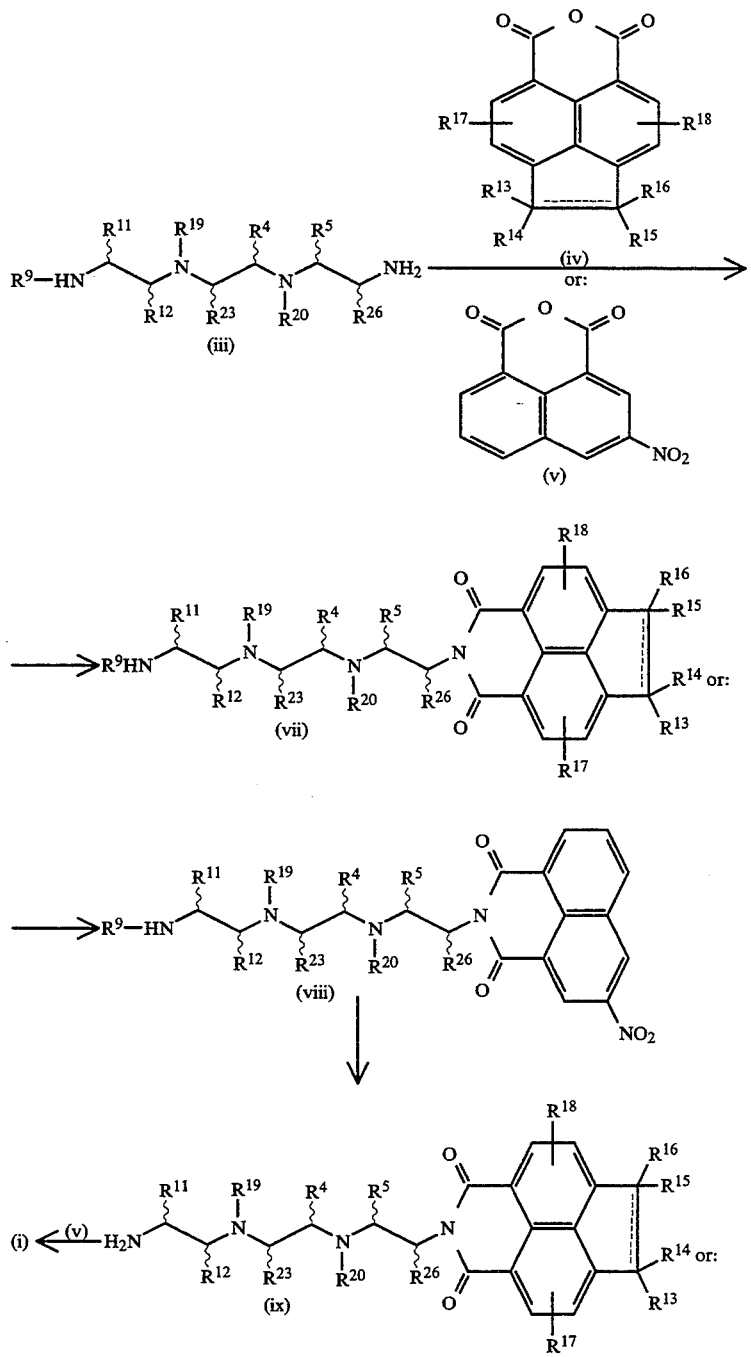

Scheme A

Scheme A

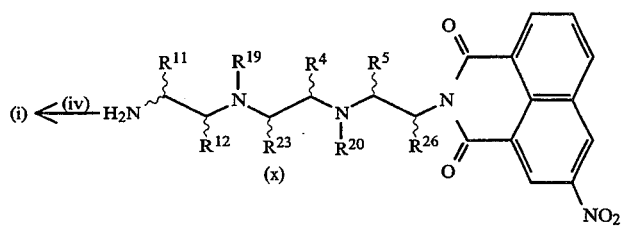

The anhydride (v), 3-nitronaphthalic anhydride, is commercially available. Polyamines of formula (iii) and anhydrides of formula (iv) can be made using the methods described further below.

In the Schemes below, the 3-nitronaphthalimide group derived from anhydride v is designated by a formula:

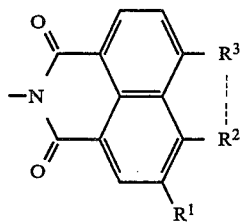

wherein $R^1$ is $NO_2$ and $R^2$ and $R^3$ are H.

In the schemes below, the imide group derived from anhydride iv is designated by a formula:

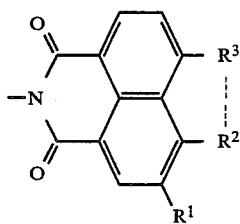

wherein $R^1$ is H and $R^2$ and $R^3$ are $CH_2$ or $C(R^{13})(R^{14})C(R^{15})(R^{16})$.

The compounds of the present invention of formula (i) can be synthesized using procedures similar to those specific procedures described below for representative compounds of formula (i).

The synthesis of compounds of representative compounds of formula (i), wherein $R^{11}=R^{26}=CH_3$, $R^{12}=R^{23}=R^4=R^5=R^{13}=R^{14}=R^{15}=R^{16}=R^{17}=R^{18}=H$ can be produced, as shown in Scheme I, through the utility of a differentially protected linker. The synthesis begins with the 1,1'-carbonyldiimidazole (CDI) coupling of N-mesitylenesulfonyl-D-alanine (II) (Ger. Patent DE 2544859, 1976) and N-tert-butoxycarbonyl-1,2-ethanediamine (Krapcho, Syn.Comm. 1990, 20 (16), 2559) to yield the amide III. The t-butyl carbonate (BOC) protecting group of amide III was then removed under acidic conditions, and the resulting salt was treated with sodium carbonate to afford the free base IV. This material was then subjected to a CDI coupling with N-BOC-D-alanine, acid removal of the BOC group, and subsequent treatment with sodium carbonate to yield the diamide VI. The amide bonds of VI were reduced with $BH_3$.THF to provide the key differentially protected linker VII, which was then condensed with the anhydride v (or anhydride vi, 6,7-dihydroacenaphtho[5,6-cd]pyran-1,3-dione, which is prepared by literature reference: Wyler, M.; Kershaw, A., U.S. Pat. No. 2,072,237 Mar. 2, 1937), to yield the mono-imide VIII (or IX). At this point, the mesitylenesulfonyl group was removed with 30% HBr/acetic acid to afford the crystalline salt Xb (or XIb). Treatment with sodium carbonate gave the freebase, which was condensed with the appropriate anhydride v (or vi) to give the freebase Ia. This free base can be acidified with the appropriate mineral or organic acid as described above to produce a pharmaceutically acceptable salt Ib.

Scheme I

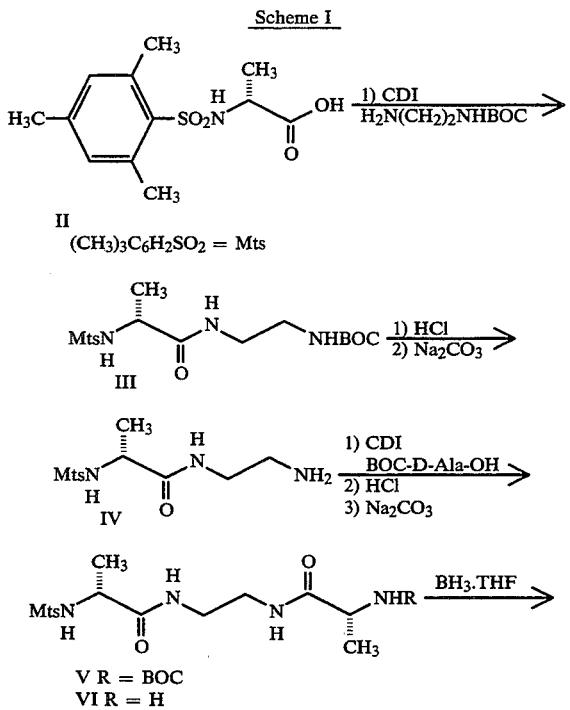

-continued
Scheme I

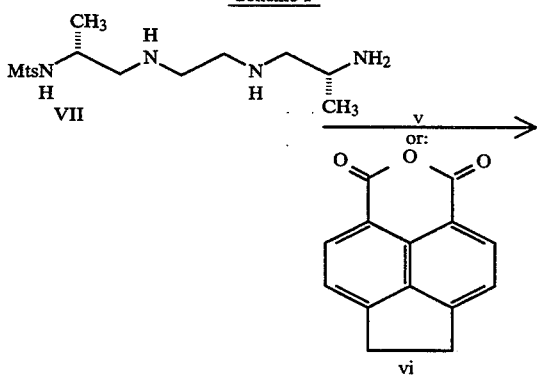

In addition to the above, compounds of formula I where $R^{11}=R^{26}=CH_3$ and $R^{12}=R^{23}=R^4=R^5=R^{13}=R^{14}=R^{15}=R^{16}=R^{17}=R^{18}=H$ can also be produced from a selective condensation as shown in Scheme II. Starting with the polyamine XII (Sun PCT US92/17453), a selective condensation with the anhydride v (or vi) gives the previously made mono-imide Xa (or XIa). This material can then be converted, as before (Scheme I), to the desired bis-imide Ib Scheme II

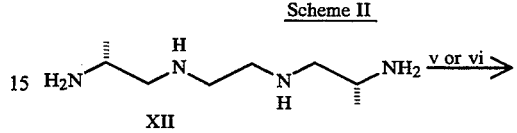

Bis-imides of the formula XX where $R^{12}=R^5=CH_3$, and $R^{11}=R^{23}=R^4=R^{26}=R^{13}=R^{14}=R^{15}=R^{16}=R^{17}=R^{18}=H$ can be made as shown in Scheme III. The BOC protected diamine XIII (PCT patent application WO 8504403 A1) can be protected as the mesitylenesulfonyl amide prior to BOC removal giving the sulfonamide XIV. This material can be coupled with methyl oxalyl chloride and saponified to provide the acid amide XV. A second coupling with alaninamide provides the diamide XVI, which is reduced with borane to the amine XVII. The first condensation with anhydride vi (or v) furnishes the mono-imide XVIII (or XIX). The standard HBr/acetic acid deprotection is followed by the second condensation with anhydride v (or vi) to provide the desired bis-imide XX.

Scheme III

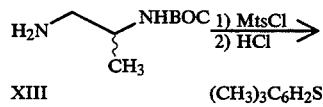
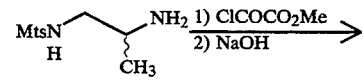

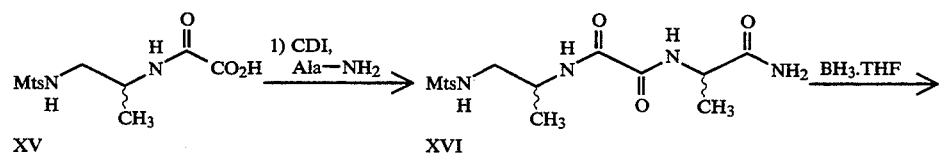

Scheme III -continued

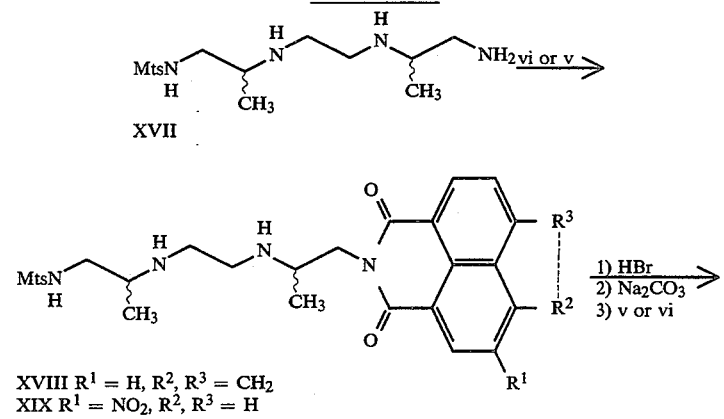

XVIII R¹ = H, R², R³ = CH₂
XIX R¹ = NO₂, R², R³ = H

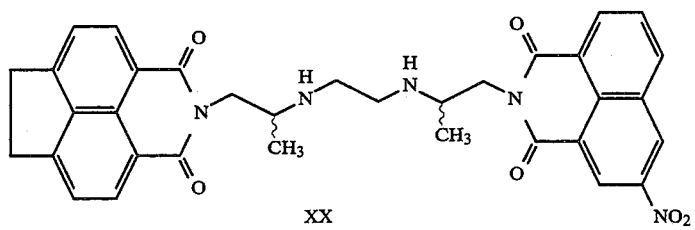

XX

Bis-imides of the formula XXIX and XXX where $R^{12}=R^5=R^{13}=R^{14}=R^{15}=R^{16}=R^{17}=R^{18}=H$, $R^{11}=R^{26}=CH_3$, and $R^{23}$ or $R^4=CH_3$ can be prepared as shown in Scheme IV. As before, N-mesitylenesulfonyl-alanine II can be homologated under standard conditions with ammonia followed by reduction with BH₃.THF to provide the amine XXI. Coupling to BOC-alanine with CDI followed by deprotection of the BOC protecting group, gives the amide XXII. The linker is completed by another BOC-alanine coupling/BOC deprotection sequence to provide the diamide XXIII. This material can then be reduced under the standard borane conditions to give the triamine XXIV.

Scheme IV

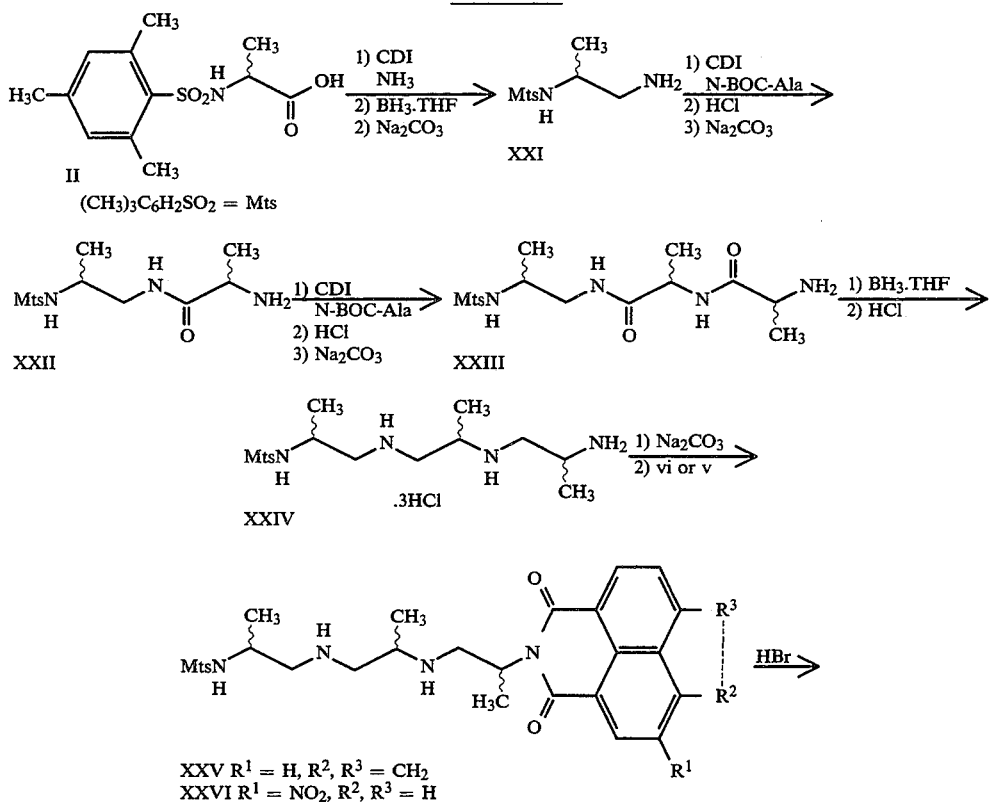

XXV R¹ = H, R², R³ = CH₂
XXVI R¹ = NO₂, R², R³ = H

-continued
Scheme IV

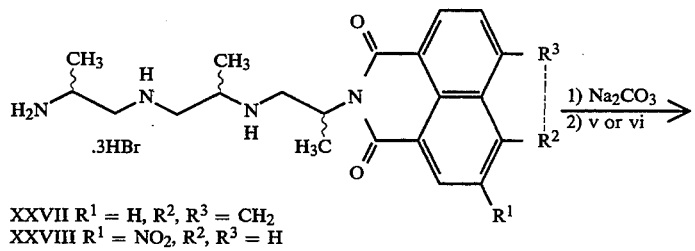

XXVII R[1] = H, R[2], R[3] = CH$_2$
XXVIII R[1] = NO$_2$, R[2], R[3] = H

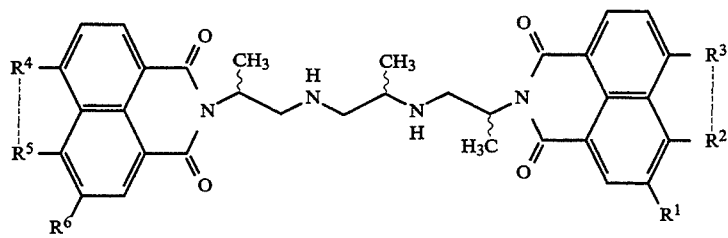

XXIX R[1] = H, R[2], R[3] = CH$_2$; R[4], R[5] = H, R[6] = NO$_2$
XXX R[1] = NO$_2$, R[2], R[3] = H; R[4], R[5] = CH$_2$, R[6] = H

The first imide (the mono-imide) can be made by condensation of the primary amine with anhydride vi or v yielding the mono-imide XXV or XXVI. Deprotection of the mesitylenesulfonyl protecting group with HBr/acetic acid can give the primary amine XXVII or XXVIII. The synthesis can be completed by a second condensation with v or vi to yield the desired unsymmetrical bis-imide XXIX or XXX.

Bis-imides of the formula XXXVIII or XXXIX where
R[12]=R[26]=R[13]=R[14]=R[15]=R[16]=R[17]=R[18]=H,
R[11]=R[5]=CH$_3$, and R[23] or mesitylenesulfonyl-alanine (II) (Scheme V).

Scheme V

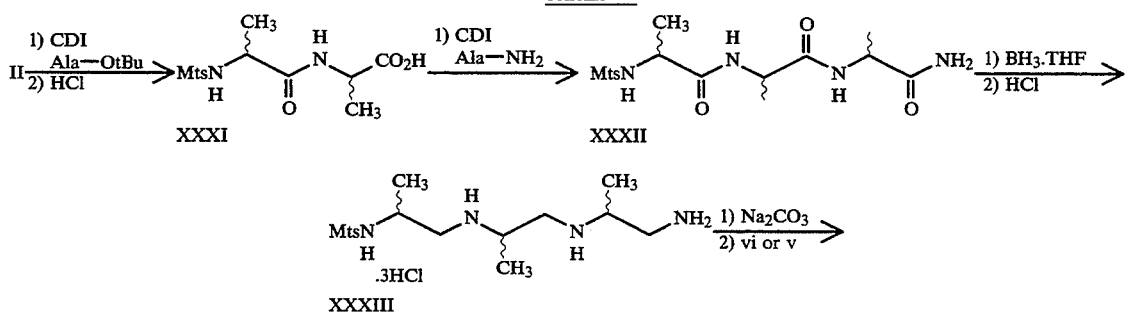

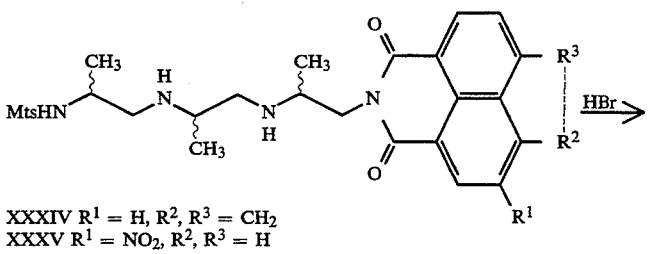

XXXIV R[1] = H, R[2], R[3] = CH$_2$
XXXV R[1] = NO$_2$, R[2], R[3] = H

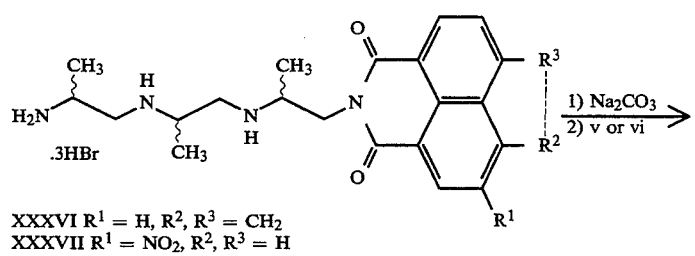

XXXVI R[1] = H, R[2], R[3] = CH$_2$
XXXVII R[1] = NO$_2$, R[2], R[3] = H

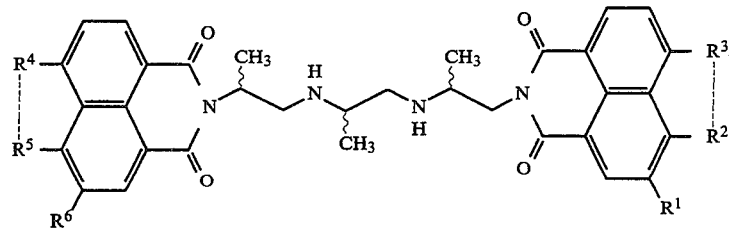

XXXVIII R$^1$ = H, R$^2$, R$^3$ = CH$_2$; R$^4$, R$^5$ = H, R$^6$ = NO$_2$
XXXIX R$^1$ = NO$_2$, R$^2$, R$^3$ = H; R$^4$, R$^5$ = CH$_2$, R$^6$ = H

Standard CDI coupling of BOC-alanine and II followed by deprotection of the BOC group gives the amide XXXI. Another CDI coupling with alaninamide gives the triamide XXXII. Borane reduction gives the differentially protected linker XXXIII. The freebase of which can be condensed with anhydride vi (or v) to give the mono-imide XXXIV (or XXXV). Deprotection with HBr/AcOH provides the mono-imide salt XXXVI (or XXXVII). A second condensation with anhydride v (or vi) gives the desired unsymmetrical bis-imide XXXVIII or XXXIX.

Bis-imides of the formula XXXXX or XXXXXI where R$^{11}$=R$^{26}$=R$^{13}$=R$^{14}$=R$^{15}$=R$^{16}$=R$^{17}$=R$^{18}$=H, R$^{12}$=R$^5$=CH$_3$, and R$^{23}$ or R$^4$=CH$_3$ can be made as shown in Scheme VI. The BOC protected diamine XIII (PCT patent application WO 8504403 A1) is converted into the mesitylenesulfonyl amine XXXXI under standard conditions. Lactic acid XXXXII can be converted to the t-butyl ester triflate XXXXIII and coupled with XXXXI, using chemistry described by Webb et. al., (J. Org. Chem., p.4706 (1991)) to provide the amine XXXXIV. BOC deprotection, followed by CDI coupling with alaninamide can provide the diamide XXXXVI. Reduction of the diamide with borane provides the differentially protected polyamine linker XXXXVII. This material can then be taken through the anhydride (vi or v) condensation-HBr/acetic acid deprotection sequence to yield mono-imide XXXXVIII (or XXXXIX). A second anhydride (v or vi) condensation provides the desired unsymmetrical bis-imide XXXXX or XXXXXI.

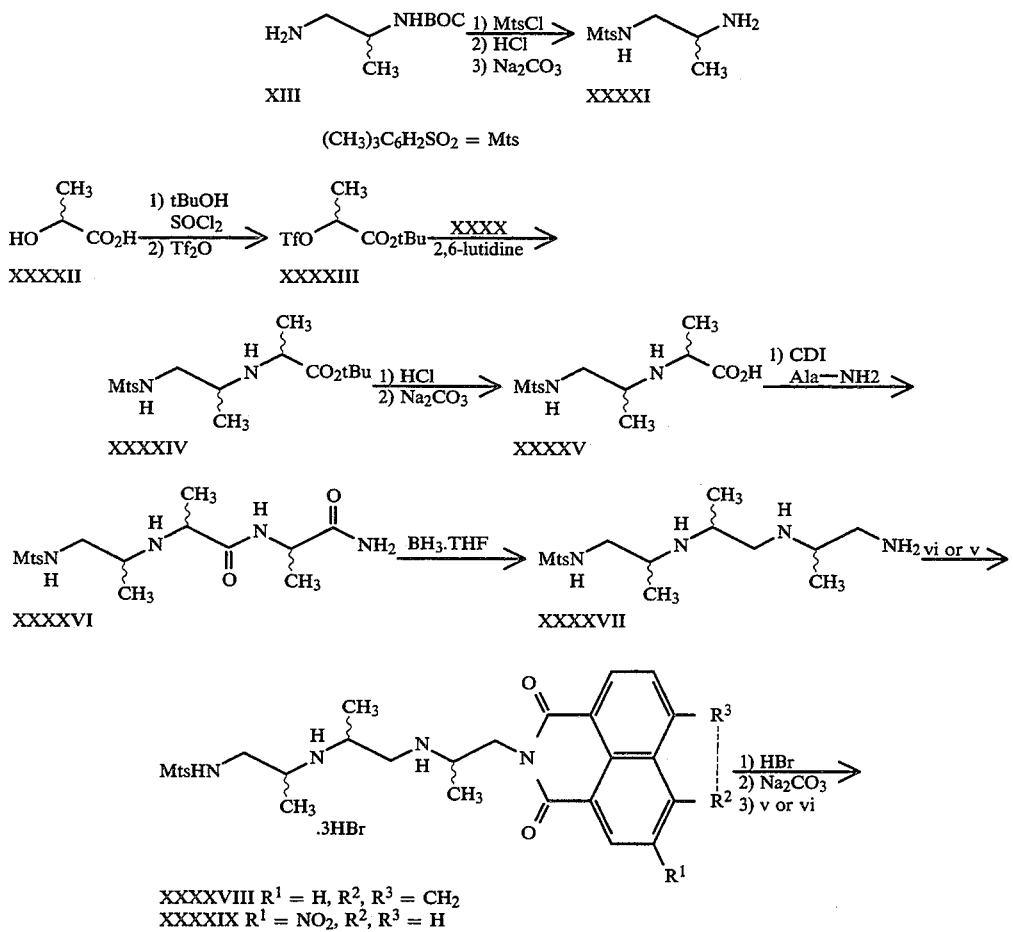

XXXXVIII R$^1$ = H, R$^2$, R$^3$ = CH$_2$
XXXXIX R$^1$ = NO$_2$, R$^2$, R$^3$ = H

-continued

Scheme VI

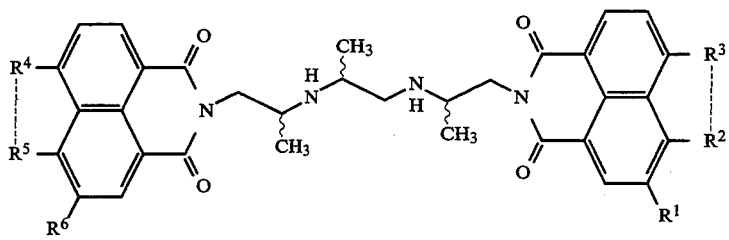

XXXXX $R^1$ = H, $R^2$, $R^3$ = $CH_2$; $R^4$, $R^5$ = H, $R^6$ = $NO_2$
XXXXXI $R^1$ = $NO_2$, $R^2$, $R^3$ = H; $R^4$, $R^5$ = $CH_2$, $R^6$ = H

The polyamines described in Schemes I-VI have only been depicted alanine ($R^{11}$, $R^{12}$, $R^{23}$, $R^4$, $R^5$, and $R^{26}$=$CH_3$) case. The ethyl substituted polyamine linker ($R^{11}$, $R^{12}$, $R^{23}$, $R^4$, $R^5$, and $R^{26}$=ethyl) can be obtained using the procedures described above using 2-amino butyric acid in place of alanine.

The polyamines shown above can be coupled with a variety of anhydrides of general formula (iv). A representative list of examples of compounds of the present invention are shown in Table I. Many of the requisite anhydrides are available from electrophilic additions (Eckert and Fisher U.S. Pat. No. 2,067,138) onto the parent anhydride (vi), acenaphthalic acid anhydride. In this manner, the 3-sulfo, 3-nitro, 3-iodo, 3-fluoro, and 3-formylacenaphthalic acid anhydrides are available. From these derivatives, using standard chemistry, one may also obtain the 3-amino, 3-N-alkylamino, 3-cyano, 3-ethenyl, 3-alkoxy, 3-aryl, and 3-trihalomethylacenaphthalic acid anhydrides. The unsaturated anhydride, 5,6-acenaphthylenedicarboxylic anhydride, is also known along with the 1,2-dibromo-5,6-acenaphthylene- dicarboxylic anhydride (Trost et. al. *J. Org. Chem.*, p.2620 (1967) and *J. Amer. Chem. Soc.,* p. 918, (1969)). The 1,2-dibromo derivative can be substituted using standard chemistry (Stille *Angew. Chem. Int. Ed. Engl.,* p.508 (1986)) to yield the 1,2-dicarbomethoxy, 1,2-dicyano, 1,2-dialkenyl, 1,2-dialkyl, 1,2-diaryl, 1,2-dihalo, and the 1,2-dialkylamino-5,6-acenaphthylenedicarboxylic anhydride. The 1-substituted and 1,1-disubstituted acenaphthalic acid anhydrides, such as those required for Example 13, 14, and 15 can be obtained by similar methods as those described, from the parent anhydride (vi) after benzylic bromination.

Representative compounds of the present invention are listed below in Table I.

TABLE I

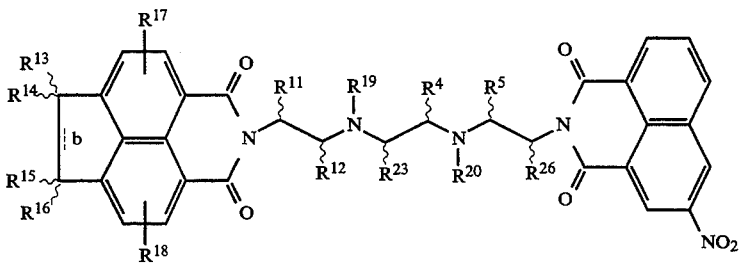

$R^{19}$ = $R^{20}$ = H

| Ex. No. | $R^{13}$ | $R^{14}$ | $R^{15}$ | $R^{16}$ | $R^{17}$ | $R^{18}$ | $R^{11}$ | $R^{12}$ | $R^{23}$ | $R^4$ | $R^5$ | $R^{26}$ |
|---|---|---|---|---|---|---|---|---|---|---|---|---|
| 1 | H | H | H | H | H | H | $CH_3$ | H | H | H | H | $CH_3$ |
| 2 | H | H | H | H | H | H | $CH_3$ | H | $CH_3$ | H | H | $CH_3$ |
| 3 | H | H | H | H | H | H | $CH_3$ | H | H | H | H | H |
| 4 | H | H | H | H | H | H | H | $CH_3$ | H | H | H | $CH_3$ |
| 5 | H | H | H | H | CN | H | $CH_3$ | H | H | H | H | $CH_3$ |
| 6 | H | H | H | H | F | H | $CH_3$ | H | H | H | H | $CH_3$ |
| 7 | H | H | H | H | $NH_2$ | H | $CH_3$ | H | H | H | H | $CH_3$ |
| 8 | H | H | H | H | $NO_2$ | H | $CH_3$ | H | H | H | H | $CH_3$ |
| 9 | H | H | H | H | I | H | $CH_3$ | H | H | H | H | $CH_3$ |
| 10 | H | H | H | H | $CF_3$ | H | $CH_3$ | H | H | H | H | $CH_3$ |
| 11 | H | H | H | H | $NO_2$ | $NO_2$ | $CH_3$ | H | H | H | H | $CH_3$ |
| 12 | H | H | H | H | $NMe_2$ | H | $CH_3$ | H | H | H | H | $CH_3$ |
| 13 | $CH_3$ | H | H | H | H | H | $CH_3$ | H | H | H | H | $CH_3$ |
| 14 | $CH_3$ | $CH_3$ | H | H | H | H | $CH_3$ | H | H | H | H | $CH_3$ |
| 15 | CN | CN | H | H | H | H | $CH_3$ | H | H | H | H | $CH_3$ |
| 16 | H | H | H | H | Ph | H | $CH_3$ | H | H | H | H | H |
| 17 | F | F | H | H | $NO_2$ | H | $CH_3$ | H | H | H | H | $CH_3$ |
| 18* | H | — | H | — | H | H | $CH_3$ | H | H | H | H | $CH_3$ |
| 19* | Br | — | Br | — | H | H | $CH_3$ | H | H | H | H | $CH_3$ |
| 20* | $CH_2CH_3$ | — | $CH_2CH_3$ | — | H | H | $CH_3$ | H | H | H | H | $CH_3$ |
| 21* | $CH_3$ | — | $CH_3$ | — | H | H | $CH_3$ | H | H | H | H | $CH_3$ |
| 22 | H | H | H | H | H | H | Et | H | H | H | H | Et |

TABLE I-continued

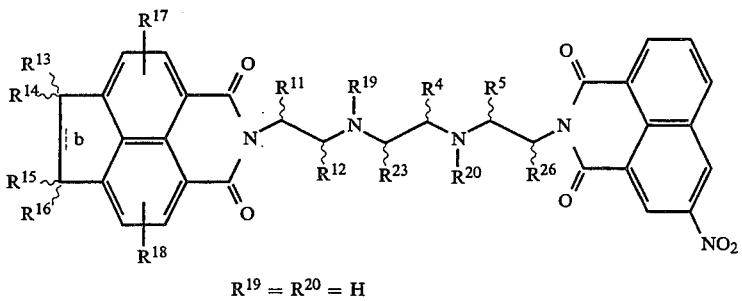

| Ex. No. | R13 | R14 | R15 | R16 | R17 | R18 | R11 | R12 | R23 | R4 | R5 | R26 |
|---|---|---|---|---|---|---|---|---|---|---|---|---|
| 23 | H | H | H | H | H | H | Et | H | H | H | H | H |

*b is double bond
Et = ethyl

The compounds of this invention and their preparation are further understood by the detailed description of the following representative Example.

EXAMPLE 1

(R,R)-1-[2-(acenaphthene-5,6-dicarboximido) propylamino]-2-[2-(3-nitronaphthalene-1,8-dicarboximido) propylamino]ethane bis-methanesulfonate (Ib)

The synthesis of Example 1 is outlined in Scheme I above.

Part A:
$N^1$-[2-(N-2,4,6-trimethylbenzenesulfonylamino)1-oxopropyl]-$N^2$-[N-1,1-dimthylethylcarbamate]-1,2-ethanediamine (III)

Mesitylenesulfonyl-D-alanine II (39.7 g, 140 mmol) was dissolved in 500 mL of methylene chloride and cooled to 0° C. prior to the addition of CDI (25.8 g, 160 mmol). After 2 h at 0° C, N-tert-butoxycarbonyl-1,2-ethanediamine (21. 3 g, 130 mmol) in 10 mL of methylene chloride was added. The solution warmed to room temperature and stirred 12 h. The solution was then washed with saturated $Na_2CO_3$, $H_2O$, and 2% HCl. The methylene chloride was dried with anhydrous $MgSO_4$ and concentrated under reduced pressure to give 43.3 g (80%) of the amide III as a white foam. $^1$H-NMR (300 MHz, $CDCl_3$) δ 6.96 (s, 2H, aromatic), 6.90 (broad s, 1H, NH), 5.65 (broad d, 1H, NH), 5.05 (broad s, 1H, NH), 3.67 (m, 1H, CH), 3.22 (m, 4H, $CH_2$), 2.63 (s, 6H, $CH_3$), 2.30 (s, 3H, $CH_3$), 1.43 (s, 9H, $CH_2$), 1.26 (d, 3H, $CH_3$); MS (CI, $NH_3$) m/e 414 (M+1).

Part B:
$N^1$-[2-(N-2,4,6-trimethylbenzenesulfonylamino)-1-oxopropyl]-1,2-ethanediamine (IV)

The amide III (60.3 g, 146 mmol) was dissolved in 150 mL of dioxane and cooled in an ice bath prior to the addition of 210 mL (840 mmol) of a 4M solution of HCl in dioxane. The solution was warmed to room temperature and stirred for 4 h. The solvent was then removed under reduced pressure to give a solid, which was dissolved in 300 mL of saturated $Na_2CO_3$ and extracted with methylene chloride. The methylene chloride was dried with $Na_2CO_3$ and was concentrated under reduced pressure to give 37.6 g (89%) of the free base IV as a white foam. $^1$H-NMR (300 MHz, $CDCl_3$) δ 7.06 (m, 1H, 1 NH), 6.95 (s, 2H, aromatic), 3.68–3.57 (m, 1H), 3.26 (m, 2H, $CH_2$), 2.79 (t, 2H, $CH_2$), 2.62 (s, 6H, 2 $CH_3$), 2.30 (s, 3H, 1 $CH_3$), 1.22 (d, 3H, 1 $CH_3$); MS (CI, $NH_3$) m/e 314 (M+1).

Part C:
1-[2-(N-2,4,6-trimethylbenzenesulfonylamino)-1-oxopropylamino]-2-[2-(N-1,1-dimthylethylcarbamate)-1-oxopropylamino]ethane (V)

The protected amino acid N-BOC-D-Ala (22.9 g, 120 mmol) was dissolved in 400 mL of methylene chloride and cooled to 0° C. prior to the addition of CDI (19.6 g, 120 mmol). The resulting mixture stirred 2 h at 0° C. before the amine IV (35.4 g, 110 mmol) suspended in 200 mL of methylene chloride was added dropwise. This mixture then warmed to room temperature and stirred 15 h. The solution was then washed with saturated $Na_2CO_3$, $H_2O$, and 2% HCl. The methylene chloride was dried with anhydrous $MgSO_4$ and concentrated under reduced pressure to give 41.2 g of the diamide V as a white foam. $^1$H-NMR (300 MHz, $CDCl_3$) δ 7.14 (broad s, 1H, NH), 6.96 (s, 2H, aromatic), 6.83 (broad s, 1H, NH), 5.92 (broad s, 1H, NH), 5.31 (broad s, 1H, NH), 4.10 (m, 1H, CH), 3.71 (m, 1H, CH), 3.4–3.2 (m, 2H, $CH_2$), 2.63 (s, 6H, $CH_3$), 2.30 (s, 3H, $CH_3$), 1.43 (s, 9H, $CH_3$), 1.22 (d, 3H, $CH_3$); MS (CI,$NH_3$) m/e 485 (M+1).

Part D:
1-[2-(N-2,4,6-trimethylbenzenesulfonylamino)-1-oxopropylamino]-2-[2-amino-1-oxopropylamino]ethane (VI)

The diamide V (41.2 g, 85 mmol) was dissolved in 10 mL of dioxane and cooled in an ice bath prior to the addition of 129 mL (510 mmol) of a 4M solution of HCl in dioxane. The solution was warmed to room temperature and stirred for 4 h. The solvent was then removed to give a solid, which was dissolved in 300 mL of saturated $Na_2CO_3$ and extracted with methylene chloride. The methylene chloride was dried with $Na_2CO_3$ and concentrated under reduced pressure to give 22.8 g (70%) of the free base VI as a white solid. $^1$H-NMR (300 MHz, $CDCl_3$) δ 7.68 (broad m, 1H, NH), 7.18 (broad m, 1H, NH), 6.96 (s, 2H, aromatic), 3.66 (m, 1H), 3.50–3.25 (m, 5H), 2.63 (s, 6H, $CH_3$), 2.3 (s, 3H, $CH_3$), 1.31 (d, 3H, $CH_3$), 1.23 (d, 3H, $CH_3$); MS (CI,$NH_3$); m/e 385 (M+1).

Part E:
1-[2-(N-2,4,6-trimethylbenzenesulfonylamino)-1-oxo-propylamino]-2-[2-amino-1-oxopropylamino]ethane (VII)

The free amine VI (22.8 g, 59.4 mmol) was dissolved in 200 mL of THF prior to the addition of 1M BH$_3$.THF (594 mL, 594 mmol). This solution was refluxed for 15 h. After cooling, 200 mL of methanol was added, and the solution was refluxed an additional 4 h. The solution was then cooled and concentrated under reduced pressure. The resulting residue was dissolved in 150 mL of MeOH and cooled to 0° C. prior to the addition of 6 mL of concentrated HCl. This solution was concentrated under reduced pressure to a white solid, which was dissolved in saturated Na$_2$CO$_3$ and extracted with methylene chloride. The methylene chloride was dried with Na$_2$CO$_3$, and concentrated under reduced pressure to give 22.1 g (93%) of the free base VII as a white foam. $^1$H-NMR (300 MHz, CDCl$_3$) δ 6.94 (s, 2H, aromatic), 3.63 (t, 1H), 3.23–3.17 (m, 1H), 2.99–2.93 (m, 1H), 2.68–2.3 (m, 8H), 2.66 (s, 6H, CH$_3$), 2.29 (s, 3H, CH$_3$), 1.6–1.5 (m, 1H), 1.43–1.3 (m, 1H), 1.06 (t, 6H, CH$_3$), 0.92 (t, 1H); MS (CI,NH$_3$) m/e 357 (M+1).

Part F: 1-[2-(N-2,4,6-trimethylbenzenesulfonylamino) propylamino]-2-[2-(3-nitronaphthalene-1,8-dicarboximido) propylamino]ethane (VIII)

The amine VII (22.1 g, 55.4 mmol) was dissolved in 500 mL of THF prior to the addition of 3-nitronaphthalic anhydride (12.0 g, 49.5 mmol), and the resulting solution was refluxed 17 h. After cooling, the solution was concentrated under reduced pressure to an oil. Flash chromatography on silica gel provided 19.3 g (66%) of the imide VIII as a foam. $^1$H-NMR (300 MHz, CDCl$_3$) δ 9.24 (d, 1H, aromatic), 9.06 (d, 1H, aromatic), 8.73 (d, 1H, aromatic), 8.38 (d, 1H, aromatic), 7.91 (t, 1H, aromatic), 6.88 (s, 2H, aromatic), 5.4 (m, 1H, CH), 3.59 (m, 1H, CH), 3.12 (m, 1H, CH), 3.01 (m, 1H, CH), 2.82 (m, 1H, CH), 2.70 (m, 1H, CH), 2.56–2.45 (m, 4H, CH$_2$), 2.52 (s, 6H, CH$_3$), 2.27 (d, 3H, CH$_3$), 1.58 (d, 3H, CH$_3$), 0.92 (d, 3H, CH$_3$); MS (CI,NH$_3$) m/e 582 (M+1).

Part G: 1-[2-amino-propylamino]-2-[2-(3-nitronaphthalene-1,8-dicarboximido) propylamino]ethane trihydrogenbromide (Xb)

The imide VIII (13.2 g, 22.7 mmol) was dissolved in 250 mL of 30% HBr/acetic acid prior to the addition of phenol (10.7 g, 113.5 mmol). This solution was heated at reflux for 4 h and then stirred at room temperature for 12 h. The solution was cooled to 0° C. and 300 mL of ether was added. The resulting solid was filtered and washed with ether to provide 12.3 g (84%) of the trihydrogen bromide salt Xb as a solid. m.p. 253°–254° C.; $^1$H-NMR (D$_2$O) δ 8.90 (d, 1H aromatic), 8.78 (d, 1H, aromatic), 8.50 (d, 1H, aromatic), 8.28 (d, 1H, aromatic), 7.76 (t, 1H, aromatic), 5.46 (m, 1H, CH), 3.90 (m, 1H), 3.64 (m, 1H), 3.5–3.18 (m, 7H), 1.56 (d, 3H, CH$_3$) and 1.27 (d, 3H, CH$_3$); MS (CI,NH$_3$) m/e 400 (free base) (M+1).

Part H: (R,R)-1-[2-(acenaphthene-5,6-dicarboximido) propylamino]-2-[2-(3-nitronaphthalene-1,8-dicarboximido) propylamino]ethane Ia The tri-hydrogen bromide salt Xb was neutralized with Na$_2$CO$_3$ to give its free base (6.35 g, 15.9 mmol), which was dissolved in 500 mL of THF. To this solution 6,7-dihydroacenaphtho [5,6-cd]pyran-1,3-dione vi (3.2 g, 14.3 mmol) was added, and the resulting solution was refluxed 15 h. After cooling, the solution was concentrated to a crude oil. Flash chromatography on silica gel provided 4.2 g (48%) of the freebase Ia as a tan foam. $^1$H-NMR (CDCl$_3$) δ 9.23 (d, 1H, 1 aromatic), 9.07 (d, 1H, aromatic), 8.71 (d, 1H, aromatic), 8.37 (t, 3H, aromatic), 7.90 (t, 1H, aromatic), 7.52 (d, 2H, aromatic), 5.23 (m, 2H, CH), 3.54 (s, 4H), 3.39 (m, 2H), 2.9 (m, 2H), 2.7 (m, 4H), 1.47 (d, 3H, CH$_3$) and 1.40 (d, 3H, CH$_3$); MS (CI,NH$_3$) m/e 606 (free base) (M+1).

Part I: (R,R)-1-[2-(acenaphthene-5,6-dicarboximido) propylamino]-2-[2-(3-nitronaphthalene-1,8-dicarboximido) propylamino]ethane bis-methanesulfonate Ib The free base Ia (3.5 g, 5.8 mmol) was dissolved in a CH$_2$Cl$_2$ (50 mL)/MeOH (80 mL) mixture prior to the addition of methanesulfonic acid (0.75 mL, 11.5 mmol). This solution was stirred 5 h. The CH$_2$Cl$_2$ was removed and MeOH added. The resulting solid was collected and dried to give the title compound Ib (2.7 g, 3.4 mmol, 58%) as a tan solid. m.p. 201°–203° C. (decomp); $^1$H-NMR (DMSO) δ 9.52 (d, 1H, 1 aromatic), 8.96 (d, 1H, aromatic), 8.82 (d, 1H, aromatic), 8.69 (d, 1H, aromatic), 8.39 (d, 2H, aromatic), 8.09 (t, 1H, aromatic), 7.70 (d, 2H, aromatic), 5.48 (m, 2H, CH), 3.86 (m, 2H), 3.57 (s, 4H), 3.36 (m, 6H), 2.23 (s, 6H), and 1.57 (d, 6H, 2CH$_3$); MS (CI,NH$_3$) m/e 606 (free base) (M+1).

Alternative synthesis of mono-imide Xa (Scheme II)

Part A:
1-[2-amino-propylamino]-2-[2-(3-nitronaphthalene-1,8-dicarboximido) propylamino]ethane (Xa)

The poylamine VII (3.0 g, 17.3 mmol) was dissolved in 150 mL of THF prior to the addition of 3-nitronaphthalic anhydride (v) (4.2 g, 17.3 mmol) at 0° C. The resulting solution was stirred at room temperature for 3 h before being refluxed for 1.5 h. After cooling, the solution was stirred at room temperature for 15 h. The reaction solution was concentrated, and chromatography provided 2.7 g (38%) of the free base Xa as a foam. $^1$H-NMR (CDCl$_3$) δ 9.29 (d, 1H, 1 aromatic), 9.11 (d, 1H, aromatic), 8.75 (dd, 1H, aromatic), 8.40 (dd, 1H, aromatic), 7.93 (t, 1H, aromatic), 5.37 (m, 1H, CH), 3.48 (dd, 1H), 3.01 (dd, 1H), 2.8–2.6 (m, 5H), 2.46 (dd, 1H), 2.24 (dd, 1H), 1.58 (d, 3H, CH$_3$) and 0.92 (d, 3H, CH$_3$); MS (CI,NH$_3$) m/e 400 (M+1).

UTILITY

In vitro Growth Inhibitory Activity

L1210 cells were maintained in RPMI-1640 a medium supplemented with 10% heat inactivated fetal bovine serum to a final concentration of 55 μM.

Exponentially growing murine leukemia L1210 cells ($1 \times 10^3$ cells) in 0.1 mL medium were seeded on day 0 in a 96-well microtiter plate. On day 1, 0.1M aliquot of medium containing graded concentrations of test analogs was added to the initial volume. After incubation at 37° C. in a humidified incubator for 3 days, the plates were centrifuged briefly and 100 mL of the growth medium was removed.

Exponentially growing human colon Clone A cells ($8 \times 10^2$) in 0.1 mL medium were seeded on day 0 in a 96-well microtiter plate. On day 1, 0.1 mL of medium containing graded concentrations of test analogs was added to the initial volume. After incubation at 37° C. in a humidified incubator for 6 days, the plates were centrifuged briefly and 0.1 mL of the growth medium was removed.

The cell cultures (above) were then incubated with 50 μL of 3-(4,5-dimethylthiazol-2-yl)-2,5-diphenyltetrazolium bromide (MTT; 1 mg/ml in Dulbecco's phosphate buffer saline) for 4 hours at 37° C. The resulting purple formazan precipitate was solubilized with 200 μL of 0.04N HCl in isopropyl alcohol. Absorbance was read in a Titertek Multiskan MCC scanning well spectrophotometer (Flow Laboratories) at a test wavelength of 570 nm and a reference wavelength of 630 nm.

The $ID_{50}$ values were determined by a computer program that fit all of the data (8 determinations per concentration and 12 concentrations per test analog) to the following equation:

$$Y = ((Am - Ao)/(1 + (X/ID_{50})n)) + Ao$$

where: Am=absorbance of the control cells; Ao=absorbance of the cells in the presence of highest drug concentration; Y=observed absorbance; X=drug concentration; $ID_{50}$=dose of drug that inhibits the growth of cells to one half that of the control cells.

Results of the in vitro L1210 leukemia and Clone A colon carcinoma growth inhibition testing show that a representative compound of the invention, the compound of Example 1, has an $ID_{50}$ of 0.1 μg/mL and 0.058 μg/mL, respectively.

In Vivo Tumor Models

Example 1, a representative compound of the present invention, has been tested in pre-clinical tests of anti-cancer activity which are indicative of clinical utility. The potent (<0.1 μg/mL) growth inhibitory activity against L1210 leukemia and Clone A colon carcinoma cell lines suggest that the compounds of the invention have the potential to be active in in vivo models. This was confirmed, since the presently claimed compound showed striking in vivo efficacy against human tumors xenografted in nude mice.

The methods used in the testing of compounds in the in vivo human tumor xenograft models are described below.

In Vivo Human Tumor Xenograft Models

The MX-1 human mammary carcinoma and the DLD-2 human colon carcinoma were originally obtained from a surgically removed primary breast tumor and colon carcinoma, respectively. The human tumor lines were maintained by serial passage in athymic nude mice. The MX-1 human mammary carcinoma is an established tumor used by the NCI. The MX-1 and DLD-2 tumor models have been well characterized.

The mice used in these experiments were outbred Swiss mice or BALB/c mice bearing the nude (nu/nu) gene. On day 0 male and female mice weighing 20–25 g are inoculated subcutaneously with 0.2 mL of a 25% tumor mince. This mince is prepared by mincing fresh tumor tissue, grown subcutaneously in passage mice, in sterile physiological saline. Palpable tumors weighing 50–100 mg (estimated by caliper measurement as described before) appear in the mice within 7–10 days after inoculation. The mice are pair matched by tumor weight and sex into groups of ten each and the test compounds and vehicle control are administered intravenously (i.v.) once daily for nine consecutive days. Tumor measurements and body weights are recorded once a week. Fifteen to 18 days after the initial injection the mice are weighed, sacrificed and the tumors excised and weighed.

The efficacy of the test compounds is determined by the extent of tumor growth inhibition in treated versus vehicle-treated control mice. Initial tumor weights (mg) are calculated from the tumor dimensions (mm) from caliper measurements, using the formula for a prolate ellipsoid (mg of tumor weight=(length×width$^2$)/2). Net tumor weights are calculated for each of the treated groups and the vehicle-treated control group by subtracting the initial tumor weight from the final tumor weight on day 15. Results are expressed as a percentage decrease relative to the mean tumor weight for the control vehicle-treated group.

% Tumor Growth Inhibition =

$$\left[ 1 - \frac{\text{mean net tumor weight of treated}}{\text{mean net tumor weight of control}} \right] \times 100$$

Activity Criteria

The criteria of the National Cancer Institute (NCI) for activity in the in vivo cancer models were used. Tumor growth inhibition of ≧90% in the DLD-2 assay is condidered excellent, and inhibition of 58–89% is considered good activity. Compounds demonstrating <58% growth inhibition are considered inactive. Actual tumor regressions (IR=incomplete regression; FR=full regression) indicate outstanding activity.

The compound of Example 1 exhibited excellent to outstanding activity in the MX-1 human breast tumor model. In addition, the compound of Example 1 exhibited excellent to outstanding activity in the DLD-2 human colon tumor model. All of the compounds of the invention are expected to exhibit similar activity.

The demonstrated effectiveness of the compounds of the present invention in the human breast and colon tumor xenograft models indicate that the compounds of the present invention may be useful for the treatment of solid tumors in man, and, in particular, tumors of the breast and colon. This conclusion is further supported by published analyses correlating pre-clinical test results with clinical efficacy of anti-cancer agents. For example, see: Goldin and Venditti (1980) Recent Results Cancer Research 76: 176–191; Goldin et al. (1981) Eur. J. Cancer 17: 129–142; Mattern et al. (1988) Cancer and Metastasis Review 7: 263–284; Jackson et al. (1990) Cancer Investigations 8: 39–47. Based on these published analyses, the exceptional high level of antitumor activity exhibited by the presently claimed compounds provide strong evidence that the compounds claimed in present invention may have important therapeutic utility in the treatment of cancer in man.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 1 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Useful pharmaceutical dosage forms for administration of the compounds of this invention can be illustrated as follows.

Capsules

Capsules are prepared by filling standard two-piece hard gelatin capsules each with 100 milligrams of powdered active ingredient, 175 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 100 milligrams of the active ingredient. The capsules are washed and dried.

Tablets

Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstrach and 98 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

In the present disclosure it should be understood that the specified materials and conditions are important in practicing the invention but that unspecified materials and conditions are not excluded so long as they do not prevent the benefits of the invention from being realized.

What is claimed is:

1. A compound, and pharmaceutically acceptable salts thereof, having the formula (i):

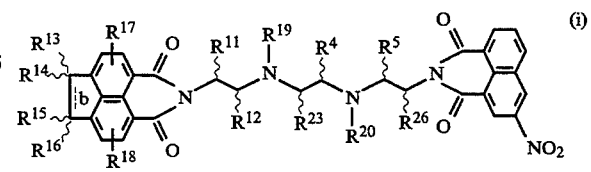

and enantiomeric or diastereomeric forms thereof, or mixtures of enantiomeric or diastereomeric forms thereof, wherein:

$R^{11}$, $R^{12}$, $R^{23}$, $R^4$, $R^5$, and $R^{26}$ are independently selected from H and $CH_3$ and $CH_2CH_3$;

$R^{19}$ and $R^{20}$ are H or $CH_3$;

$R^{18}$ is selected from: H, $C_1$–$C_6$ alkyl, $C_2$–$C_6$ alkenyl, trihalomethyl, halogen, $C_1$–$C_6$ alkoxy, hydroxy, amino, $C_1$–$C_6$ di- or mono-alkylamino, $C_1$–$C_6$ alkylcarbonyl, $C_1$–$C_7$ carboalkoxy, cyano, nitro; and $R^{13}$, $R^{15}$, $R^{17}$, $R^{14}$ and $R^{16}$ are H;

b, the bond between carbon atoms substituted with $R^{13}$ and $R^{15}$, is a single bond.

2. A compound of claim 1 wherein:

$R^{11}$, $R^{12}$, $R^{23}$, $R^4$, $R^5$, and $R^{26}$ are independently selected from H and $CH_3$ and $CH_2CH_3$;

$R^{19}$ and $R^{20}$ are H;

$R^{13}$, $R^{15}$, $R^{17}$, $R^{18}$, $R^{14}$ and $R^{16}$ are H;

b, the bond between carbon atoms substituted with $R^{13}$ and $R^{15}$, is a single bond.

3. A compound of claim 1 wherein:

$R^{11}$ and $R^{26}$ are $CH_3$;

$R^{12}$, $R^{23}$, $R^4$, and $R^5$ are H;

$R^{19}$ and $R^{20}$ are H;

b is a single bond; and $R^{13}$, $R^{14}$, $R^{15}$, $R^{16}$, $R^{17}$, and $R^{18}$ are H.

4. A compound of claim 2 selected from the following compounds, and pharmaceutically acceptable salts thereof:

(R,R)-1-[2-(acenaphthene-5,6-dicarboximido) propylamino]-2-[2-(3-nitronaphthalene-1,8-dicarboximido) propylamino]ethane;

(S,S)-1-[2-(acenaphthene-5,6-dicarboximido) propylamino]-2-[2-(3-nitronaphthalene-1,8-dicarboximido) propylamino]ethane;

(racemate+meso)-1-[2-(acenaphthene-5,6-dicarboximido) propylamino]-2-[2-(3-nitronaphthalene-1,8-dicarboximido) propylamino]ethane;

(meso)-1-[2-(acenaphthene-5,6-dicarboximido) propylamino]-2-[2-(3-nitronaphthalene-1,8-dicarboximido) propylamino]ethane.

* * * * *